United States Patent
Safai et al.

(10) Patent No.: US 10,335,838 B2
(45) Date of Patent: Jul. 2, 2019

(54) SYSTEM AND METHOD FOR HIGH SPEED FOD DETECTION

(71) Applicant: The Boeing Company, Chicago, IL (US)

(72) Inventors: Morteza Safai, Newcastle, WA (US); Jeffrey G. Thompson, Auburn, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 15/806,380

(22) Filed: Nov. 8, 2017

(65) Prior Publication Data

US 2018/0085792 A1 Mar. 29, 2018

Related U.S. Application Data

(63) Continuation of application No. 14/614,198, filed on Feb. 4, 2015, now Pat. No. 9,839,946.

(51) Int. Cl.
| | |
|---|---|
| *G06K 9/00* | (2006.01) |
| *B08B 5/02* | (2006.01) |
| *G01N 21/94* | (2006.01) |
| *G01N 21/88* | (2006.01) |
| *B29C 70/30* | (2006.01) |
| *G01N 21/84* | (2006.01) |

(52) U.S. Cl.
CPC ............... *B08B 5/02* (2013.01); *B29C 70/30* (2013.01); *G01N 21/8851* (2013.01); *G01N 21/94* (2013.01); *G01N 2021/8472* (2013.01); *G01N 2201/103* (2013.01)

(58) Field of Classification Search
CPC . G06T 2007/10048; G06T 2007/30108; G06T 7/0002; G06T 7/0006; G06T 7/0008; H04N 5/33; G01J 2005/0077; G01J 3/108
See application file for complete search history.

(56) References Cited

U.S. PATENT DOCUMENTS

| | | | |
|---|---|---|---|
| 6,112,903 A | 9/2000 | Kimmel | |
| 6,301,512 B1* | 10/2001 | Motzer | ................... A61B 8/00 345/629 |
| 7,157,714 B2 | 1/2007 | Del Grande | |
| 7,220,966 B2 | 5/2007 | Saito et al. | |
| 7,287,902 B2 | 10/2007 | Safai et al. | |
| 7,312,454 B2 | 12/2007 | Safai et al. | |
| 7,553,070 B2 | 6/2009 | Kollgaard et al. | |

(Continued)

*Primary Examiner* — Wesley J Tucker
(74) *Attorney, Agent, or Firm* — Toler Law Group, P.C.

(57) ABSTRACT

A system for the detection of foreign object debris material on a surface of a composite part being manufactured. A platform is configured to move over the surface. A thermal excitation source is fixed to the platform and configured to direct infrared radiation across the surface. An infrared camera is also fixed to the platform and configured to scan the surface as the platform moves over the surface to detect and output a signal proportional to infrared radiation emitted by the surface and/or by any foreign object debris material on the surface in response to the infrared radiation from the excitation source. A controller is coupled to the excitation source and to the infrared camera and is configured to compare the signal from the infrared camera with a first predetermined threshold signal to detect if any foreign object debris material is located on the surface.

21 Claims, 4 Drawing Sheets

(56) References Cited

U.S. PATENT DOCUMENTS

| | | | |
|---|---|---|---|
| 7,724,925 B2* | 5/2010 | Shepard | G01N 25/72 |
| | | | 382/115 |
| 8,167,482 B2 | 5/2012 | Hatcher | |
| 8,204,294 B2 | 6/2012 | Alloo et al. | |
| 8,289,372 B2 | 10/2012 | Hamrelius et al. | |
| 8,498,836 B2 | 7/2013 | Carlson | |
| 9,519,844 B1* | 12/2016 | Thompson | G06K 9/6267 |
| 2003/0179368 A1* | 9/2003 | Li | G01N 21/35 |
| | | | 356/237.2 |
| 2006/0043303 A1 | 3/2006 | Safai et al. | |
| 2013/0229516 A1* | 9/2013 | Jones | G01N 21/35 |
| | | | 348/143 |
| 2015/0161778 A1* | 6/2015 | Henderkott | G06T 7/0008 |
| | | | 348/129 |
| 2017/0138914 A1 | 5/2017 | Zhang | |

* cited by examiner

SYSTEM AND METHOD FOR HIGH SPEED FOD DETECTION

FIELD

This disclosure relates generally to a system and method for high speed foreign object debris detection, and more particularly for a system and method for detecting foreign object debris during a composite layup process.

BACKGROUND

Composite materials are increasingly used as substitutes for conventional materials such as aluminum and steel alloys in various structural components due to the generally high strength-to-weight ratio inherent in composite materials. Composite materials may generally be comprised of a network of reinforcing fibers that are generally applied in layers, and a polymeric resin that substantially wets the reinforcing fibers to form an intimate contact between the resin and the reinforcing fibers. High speed composite layup machines are typically used to form each layer. Such machines can lay composite material at a rate of 3000 inches per minute.

A problem can arise, however, when foreign object debris (FOD) or contamination is on or within the formed composite part prior to curing. For example, small amounts of entrapped or surface-adhering moisture or other types of contamination can result in delaminating and porosity of the composite material once the curing is completed. In addition, debris such as small pieces of bagging materials, Teflon tapes or breathing material used during the composite layup that becomes entrapped within a composite layer can result in delamination, porosity and wrinkles in the composite part. FOD detection is currently done manually by visual inspection. Often, however, FODs are either transparent or blend well with a surface color of the composite material and are thus difficult to detect visually. This manual FOD detection method is thus slow and unreliable. Significantly, if the FOD materials are not detected and removed prior to curing, large and expensive composite parts may be rejected during nondestructive testing.

One-piece composite parts are presently used in many applications, including parts for commercial aircraft. Such parts can be very expensive to manufacture, and very small FOD materials or contamination not removed during the buildup phase of such a part can result in a manufacturing defect that requires the rejection of the entire part. The rejection of such parts is thus quite costly and can also result in schedule delays and inventory problems.

Accordingly, there is a need for an automated high-speed inspection system for the detection and removal of FODs and other contamination during the high-speed composite layup process.

SUMMARY

In one aspect, a system for the detection of foreign object debris material on a surface. The system includes a platform configured to move over the surface. A thermal excitation source is fixed to the platform and configured to direct infrared radiation across the surface. An infrared camera is fixed to the platform and configured to scan the surface as the platform moves over the surface to detect and output a signal proportional to infrared radiation emitted by the surface and/or by any foreign object debris material on the surface in response to the infrared radiation from the excitation source. A controller is coupled to the excitation source and to the infrared camera and is configured to compare the signal from the infrared camera with a first predetermined threshold signal to detect if any foreign object debris material is located on the surface.

In a further embodiment, the system includes a high pressure air source and an associated controllable air pressure nozzle. The controllable air pressure nozzle is mounted on the platform and directed at the surface. The controller is further coupled to the controllable air pressure nozzle and configured to activate the controllable air pressure nozzle upon the detection that foreign object debris material is located on the surface.

In an alternative embodiment, a terminal which includes a display is coupled to the controller. The controller is further configured to provide an indication on the display upon the detection that foreign object debris material is located on the surface.

In another further embodiment, an ultraviolet light source is also fixed to the platform and configured to direct ultraviolet light across the surface. An ultraviolet light camera is also fixed to the platform and configured to scan the surface as the platform moves over the surface to detect and output a signal proportional to ultraviolet light reflected by the surface and/or by any foreign object debris material on the surface in response to the ultraviolet light from the ultraviolet light source. In addition, the controller is also coupled to the ultraviolet light source and to the ultraviolet light camera. The controller is also configured to compare the signal from the ultraviolet light camera with a second predetermined threshold signal to detect if any foreign object debris material is located on the surface.

In yet another further embodiment, a visible light source is also fixed to the platform and configured to direct visible light across the surface. A visible light camera is also fixed to the platform and configured to scan the surface as the platform moves over the surface to detect and output a signal proportional to visible light reflected by the surface and/or by any foreign object debris material on the surface in response to the visible light from the visible light source. The controller is also coupled to the visible light source and to the visible light camera. The controller is also configured to compare the signal from the visible light camera with a third predetermined threshold signal to detect if any foreign object debris material is located on the surface.

Preferably, the surface may be an outer surface of a composite part being formed by a composite layup machine having a head for moving over the composite part during formation thereof. The platform may be fixed to a forward portion of the head of the composite layup machine.

In a still further embodiment, a second infrared camera is also fixed to the platform and configured to scan the surface as the platform moves over the surface to detect and output a signal proportional to infrared radiation reflected by the surface and/or by any foreign object debris material on the surface in response to the infrared radiation from the excitation source. The controller is also coupled to the second infrared camera. The controller is also configured to compare the signal from the second infrared camera with a fourth predetermined threshold signal to detect if any foreign object debris material is located on the surface.

In a second aspect, a system for the detection of foreign object debris material on a surface includes a platform fixed over a movable surface. A thermal excitation source is fixed to the platform and configured to direct infrared radiation across the surface. An infrared camera is fixed to the platform and configured to scan the surface as the surface moves under the platform to detect and output a signal proportional to infrared radiation emitted by the surface and/or by any foreign object debris material on the surface in response to the infrared radiation from the excitation source. A controller is coupled to the excitation source and to the infrared camera. The controller is configured to compare the signal from the infrared camera with a first predetermined threshold signal to detect if any foreign object debris material is located on the surface.

In a further embodiment, an ultraviolet light source is also fixed to the platform and configured to direct ultraviolet light across the surface. An ultraviolet light camera is also fixed to the platform and configured to scan the surface as the surface moves under the platform to detect and output a signal proportional to ultraviolet light reflected by the surface and/or by any foreign object debris material on the surface in response to the ultraviolet light from the ultraviolet light source. The controller is also coupled to the ultraviolet light source and to the ultraviolet light camera. The controller is also configured to compare the signal from the ultraviolet light camera with a second predetermined threshold signal to detect if any foreign object debris material is located on the surface.

In another further embodiment, a visible light source is also fixed to the platform and configured to direct visible light across the surface. A visible light camera is also fixed to the platform and configured to scan the surface as the surface moves under the platform to detect and output a signal proportional to visible light reflected by the surface and/or by any foreign object debris material on the surface in response to the visible light from the visible light source. The controller is also coupled to the visible light source and to the visible light camera. The controller is also configured to compare the signal from the visible light camera with a third predetermined threshold signal to detect if any foreign object debris material is located on the surface.

In a still further embodiment, the surface is an outer surface of a composite part being formed by a composite layup machine having a head. The composite part moves under the head during formation thereof. The platform is fixed to a forward portion of the head of the composite layup machine.

In yet another further embodiment, a second infrared camera is also fixed to the platform and configured to scan the surface as the surface moves under the platform to detect and output a signal proportional to infrared radiation reflected by the surface and/or by any foreign object debris material on the surface in response to the infrared radiation from the excitation source. The controller is also coupled to the second infrared camera. The controller is also configured to compare the signal from the second infrared camera with a fourth predetermined threshold signal to detect if any foreign object debris material is located on the surface.

In a third aspect, a method for the detection of foreign object debris material on a surface. A first threshold is established for distinguishing between emitted infrared radiation from a surface of a workpiece and emitted infrared radiation from foreign object debris material on the surface of the workpiece. An infrared radiation beam from an infrared excitation source is moved over the surface of the workpiece. The surface of the of the workpiece is scanned to detect and output a signal proportional to infrared radiation emitted by the surface of the workpiece and by any foreign object debris material on the surface of the workpiece in response to the infrared radiation beam from the excitation source. The signal proportional to the infrared radiation emitted by the surface of the workpiece and by any foreign object debris material on the surface of the workpiece is compared with the first threshold to detect if any foreign object debris material is located on the surface of the workpiece.

In a further embodiment, a threshold is established for distinguishing between reflected radiation from a surface of a workpiece and reflected radiation from foreign object debris material on the surface of the workpiece. A radiation beam from a thermal excitation source is moved over the surface of the workpiece. The surface of the of the workpiece is scanned to detect and output a signal proportional to radiation reflected by the surface of the workpiece and by any foreign object debris material on the surface of the workpiece in response to the radiation beam from the excitation source. The signal proportional to the radiation reflected by the surface of the workpiece and by any foreign object debris material on the surface of the workpiece is compared with the second predetermined threshold to detect if any foreign object debris material is located on the surface of the workpiece.

The features, functions, and advantages that have been discussed can be achieved independently in various embodiments or may be combined in yet other embodiments, further details of which can be seen with reference to the following description and drawings.

BRIEF DESCRIPTION OF THE DRAWINGS

The following detailed description, given by way of example and not intended to limit the present disclosure solely thereto, will best be understood in conjunction with the accompanying drawings in which.

DETAILED DESCRIPTION

In the present disclosure, like reference numbers refer to like elements throughout the drawings, which illustrate various exemplary embodiments of the present disclosure.

The present disclosure describes a system and method for the automated inspection for foreign object debris (FOD) materials during the manufacture of large composite parts with high-speed composite layup machines. Such machines may layup composite at high speeds, for example, at a rate of 3000 inches per minute. As described in detail below, the FOD detection system and method disclosed herein employs one or more imaging cameras attached to a platform coupled to the layup machine head. In one embodiment, the FOD detection system and method of the present disclosure relies upon a single infrared camera which is preferably operable in a line scan mode. In further embodiments, the FOD detection system and method of the present disclosure may also include a visible light camera which is preferably operable in a line scan mode and/or an ultraviolet light camera which is preferably operable in a line scan mode. In order to keep up with the high speeds of the inspection layup machine, the camera (or cameras) is (are) used to create a continuous image of the surface of the composite part being manufactured and a threshold technique is used to process the continuous image to provide rapid inspection without the need for complex and time-intensive image processing.

Preferably, the FOD detection system and method of the present disclosure uses thermal excitation to enhance the detection of FOD material on the surface of the composite part being manufactured. The thermal excitation device is placed at a selected distance forward of the infrared camera on the platform so the FOD material on the surface of the composite part, if any, absorbs the heat and re-emits such heat with sufficient thermal contrast to be detected by the time the infrared camera passes over the location of such FOD material. In effect, the heated FOD material and the composite part both become active emitters. This infrared scanning technique allows for detection of FOD material that may be transparent to the visible light scanners, based on differences in heat emitted by the FOD material and the composite part.

In some cases, however, certain types of FOD material may not be detectable via the infrared camera. As a result, the FOD system and method of the present disclosure may add a visible light camera and/or an ultraviolet light camera to ensure that all of the FOD material on the composite part being manufactured is detected. In a still further embodiment, an additional infrared camera may be placed closer to the thermal excitation device to separately detect reflected infrared energy (as opposed to the emitted infrared energy created by the excitation of the FOD material by the thermal excitation device). Although the FOD system and method of the present disclosure identify FOD material or surface contamination on the composite part being manufactured, in some instances this system and method may also be used to identify FOD material buried under the surface of the composite part being manufactured.

In the presently preferred embodiment, an air pressure nozzle on the platform of the FOD detection system and method may be activated, upon detection of FOD material, to eject the FOD material off the surface of the composite part being manufactured. In a further embodiment, when FOD material is located under the surface of the composite part being manufactured, the location of such FOD material may be recorded for appropriate later action, e.g., manual inspection and/or rework.

Figure 1:
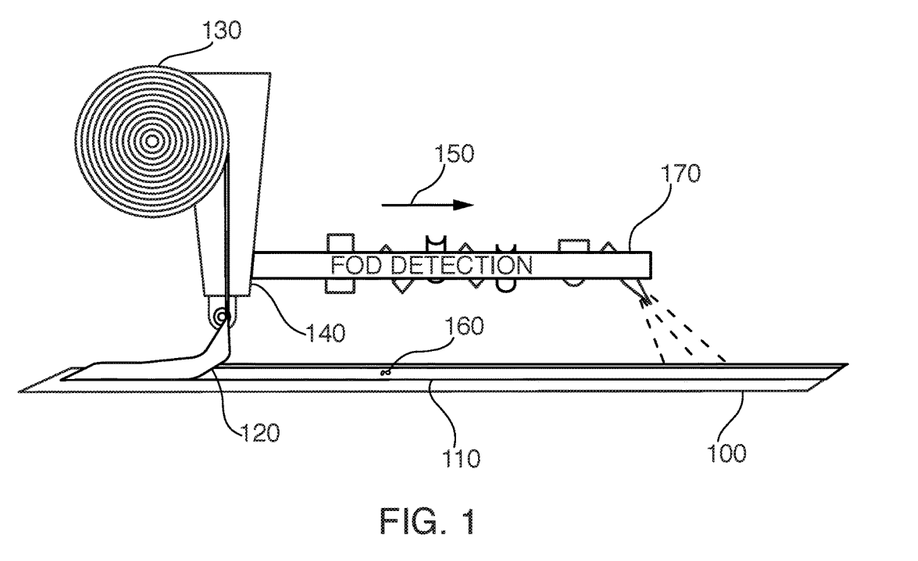
FIG. 1 is a high-level diagram of a high-speed layup machine including an FOD detection system according to the present disclosure.

Referring now to FIG. 1, a composite part 110 is formed on a base 100. A composite layup machine head 140, including a composite roll 130, moves across the composite part 110 in the direction shown by arrow 150 laying a new layer 120 of composite material over the upper surface of the composite part 110. As discussed above, significant problems can arise when FOD material, such as object 160, are located on the upper surface of the composite part 110. As a result, the present disclosure describes a FOD detection system 170 attached to the forward part of composite layup machine head 140 for detecting and removing object 160 from the surface of the composite part 110 before the new layer 120 is deposited over object 160.

Figure 2:
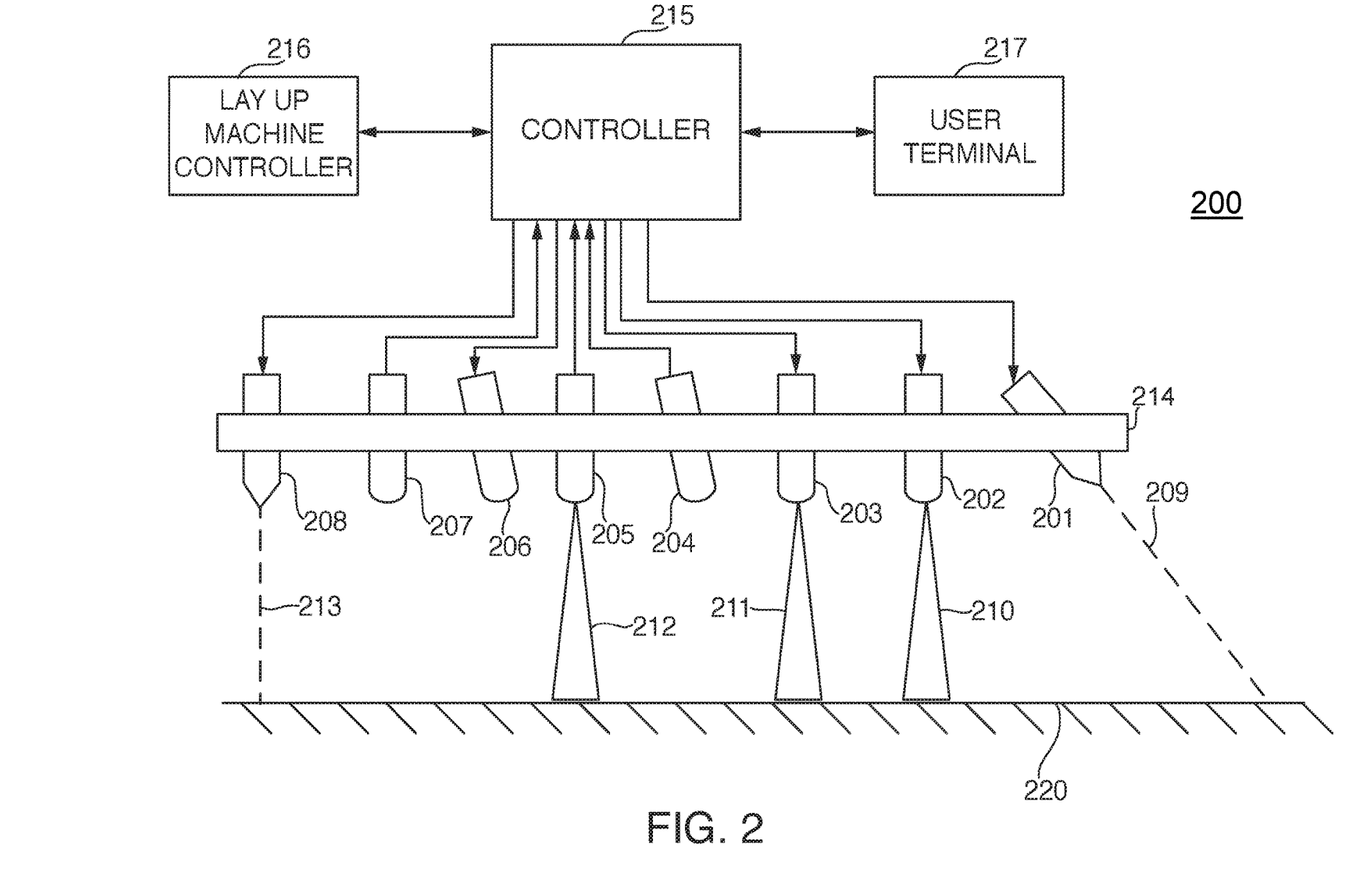
FIG. 2 is a detailed diagram of the FOD detection system shown in FIG. 1 according to the present disclosure.

The FOD detection system 170 of FIG. 1 is shown in detail in FIG. 2 as system 200. System 200 includes a platform 214 mounted to the forward edge of the composite layup machine head 140 of FIG. 1. A thermal excitation source 202 is mounted to platform 214 for exciting the work surface 220 with thermal (infrared) energy beam 210. An infrared camera 207 (or equivalent) is also mounted to platform 214 and is used to detect thermal (infrared) energy emitted from the work surface 220. As discussed below, the infrared energy emitted from a composite part being manufactured on the work surface 220 will differ from that of any FOD material present on that composite part. Thermal excitation source 202 and infrared camera 207 are both coupled to a controller 215. Controller 215 is configured to process the signals from infrared camera 207 and to detect the presence of any FOD material on the composite part based upon emitted infrared radiation. When FOD material is detected, controller 215 is configured to activate a controllable air pressure nozzle 208 (coupled to an appropriate source of high pressure air) mounted on platform 214 to direct a stream of high pressure air 213 to eject any detected FOD material off of the composite part. Controller 215 is also coupled to a user terminal 217 and may be configured to provide a signal via a display on such terminal upon the detection of any FOD material (either in addition to activating the air pressure nozzle or in the alternative thereto). As one of ordinary skill in the art will readily recognize, user terminal 217 may also be used to configure controller 215 and thus to control the operation of system 200. Controller 215 is also coupled to the layup machine controller 216 to ensure that the speed of operation of each camera, e.g., infrared camera 207, is synchronized to the speed of the composite layup machine head.

System 200 may also include an ultraviolet light illumination source 203 and an associated ultraviolet camera 204 (or equivalent) for identifying FOD material based upon reflected ultraviolet light. Ultraviolet light illumination source 203 directs a beam 211 of ultraviolet light on work surface 220. Ultraviolet light illumination source 203 and ultraviolet camera 204 are both coupled to controller 215. Controller 215 is also configured to process the signals from ultraviolet camera 204 and to detect the presence of any FOD material on the composite part based upon reflected ultraviolet light. This provides system 202 with the ability to identify FOD material which might not be detected based on emitted infrared radiation but which can be detected based on reflected ultraviolet light.

System 200 may further include a visible light illumination source 205 and an associated visible camera 206 (or equivalent) for identifying FOD material based upon reflected visible light. Visible light illumination source 205 directs a beam 212 of visible light on work surface 220. Visible light illumination source 205 and visible camera 206 are both coupled to controller 215. Controller 215 is also configured to process the signals from visible camera 206 and to detect the presence of any FOD material on the composite part based upon reflected visible light. This provides system 202 with the ability to identify FOD material which might not be detected based on emitted infrared radiation or reflected ultraviolet light but which can be detected based on reflected visible light.

A second air pressure nozzle 201 may be mounted on platform 214 to direct a stream of high pressure air 209 against surface 202 which is always active in an effort to remove FOD material from the surface prior to inspection by system 200.

Figure 3:
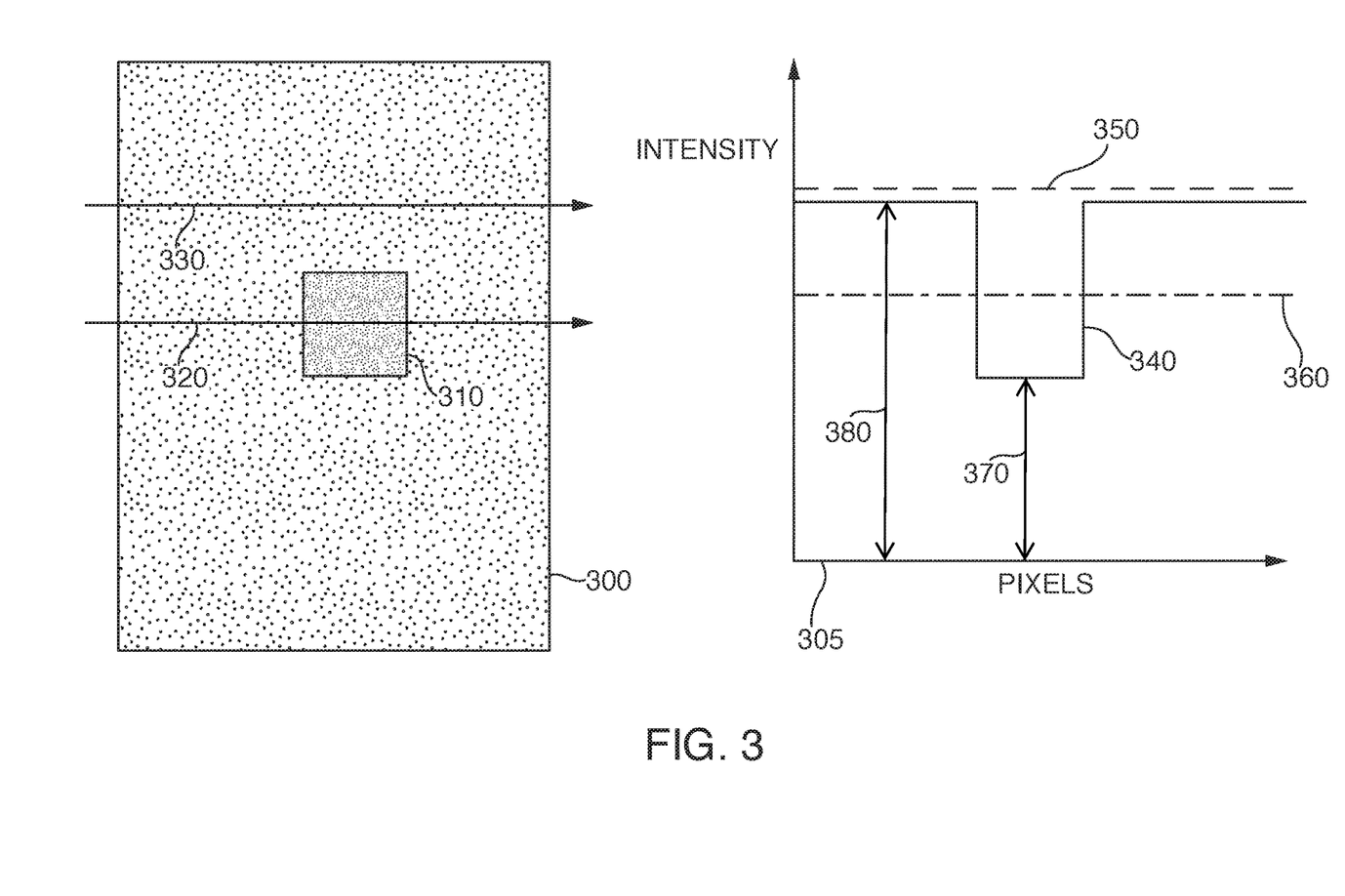
FIG. 3 illustrates one example of a threshold level for the FOD detection system of FIG. 2 according to the present disclosure.

Referring now to FIG. 3, a composite part 300 being manufactured may include FOD material 310 on the surface thereof. As shown by the differing shading in FIG. 3, the composite part 300 will have a different characteristic than the FOD material 310 (in terms of one or more of emitted infrared radiation, reflected ultraviolet light or reflected visible light). One of the cameras 204, 206, 207, will scan across composite part 300 as the platform passes over the composite part 300 (e.g., from top to bottom on FIG. 3). A first scan 330 is shown graphed in chart 305 as line 350 and a second scan 320 is shown as line 340 in chart 305. As evident, the intensity level is quite different for the FOD material 310 (level 370) than for the composite part 300 (level 380). As such, a threshold level 360 may be identified, and the FOD material 310 on composite part 300 may be identified whenever the signal from the camera 204, 206 or 207 falls below the threshold level. As one of ordinary skill in the art will readily recognize, the threshold signal level may be determined by appropriate calibration of each cameras 204, 206, 207. In addition, one of ordinary skill will readily recognize that controller 215 must be separately calibrated for each camera 204, 206, 207, setting, for example, a first threshold signal level for camera 204, a second threshold signal level for camera 206 and a third threshold signal level for camera 207. Further, one of ordinary skill will also readily recognize that in some circumstances, the intensity level for the FOD material 310 may be higher than that of the intensity level for the composite part 300, in which case FOD material 310 would be identified when the scanned intensity signal exceeds some predetermined threshold (instead of drops below the threshold as in the FIG. 3 depiction).

Figure 4:
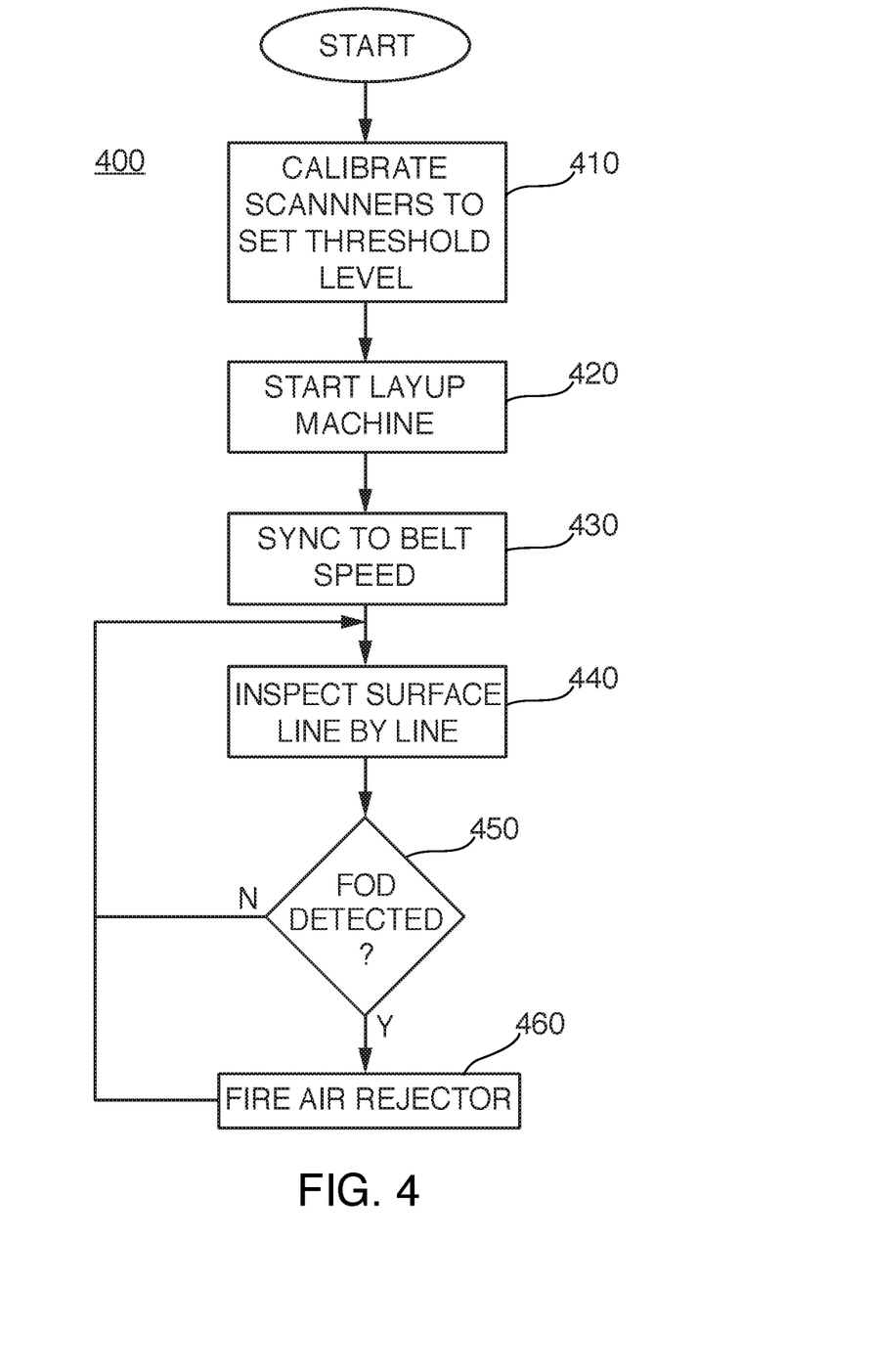
FIG. 4 is a flowchart of the operation of the FOD detection system of FIG. 2 according to the present disclosure.

Referring now to FIG. 4, a flowchart 400 showing the method of operation of system 200 in FIG. 2 is shown. As discussed with respect to FIG. 3, the first step 410 is to separately calibrate each camera 204, 206, 207 to set an appropriate threshold for each. This may be done, for example, by identifying a certain type of FOD material that can be identified for each method (i.e., emitted infrared radiation, reflected ultraviolet radiation, and reflected visible radiation) and then iteratively placing the identified FOD material on the surface of a appropriate composite part to set the threshold for each camera 204, 206, 207. As one of ordinary skill in the art will readily recognize, the threshold 360 (FIG. 3) must be set below the noise level of the composite part 300 but above the signal level of the FOD material (level 370 in FIG. 3). Once the threshold is set for each camera 204, 206, 207, the layup machine is started (step 420) and system 200 is synchronized to the belt speed of the layup machine head 140 (step 430). The synchronization is done to ensure that the line scan speed of each camera 204, 206, 207 is fast enough to identify very small FOD material on the surface of the composite part being manufactured. Once the layup machine begins operating, the surface of the composite part being manufactured is inspected line by line (step 440). This process involves monitoring the signal from each camera 204, 206, 207 to determine if that signal crosses the associated predetermined threshold level (i.e., as discussed above, in some cases FOD detection may occur when the signal exceeds the associated predetermined threshold and in other cases FOD detection may occur when the signal drops below the associated predetermined threshold) (step 450). If FOD material is detected on the surface at step 450, processing proceeds to step 460 to fire the air pressure nozzle to eject the FOD material off of the surface of the composite part being manufactured. As evident, if no FOD material is detected on the surface at step 450 or after the air pressure nozzle is fired at step 460, processing returns to step 440 to inspect the next line scan. This process continues as long as the layup machine operates.

In a further embodiment, a second infrared light camera (or equivalent) may also be mounted on platform 214 in FIG. 2 and coupled to controller 215. This second infrared light scan camera is positioned forward of infrared light camera and can be used to detect reflected (as opposed to radiated) infrared light. Controller 215 processes the signal from this second infrared light camera in the same manner as cameras 204, 206, 207, based on a predetermined fourth calibration threshold signal to identify FOD material.

In the embodiment shown in FIG. 2, platform 214 is attached to a composite layup machine head 140 (FIG. 1) which moves across a base 100 to form a composite part. As one of ordinary skill in the art will readily recognize, the system and method disclosed herein can be applied to many other types of systems where FOD detection is required. In particular, for example, in some applications platform 214 may be attached to a fixed head that is positioned over a moveable conveyor so that system 200 may detect FOD material on the surface of the conveyor.

Although the present disclosure has been particularly shown and described with reference to the preferred embodiments and various aspects thereof, it will be appreciated by those of ordinary skill in the art that various changes and modifications may be made without departing from the spirit and scope of the disclosure. It is intended that the appended claims be interpreted as including the embodiments described herein, the alternatives mentioned above, and all equivalents thereto.

What is claimed is:

1. A system for detection of foreign object debris material on a surface, the system comprising:
   a thermal excitation source configured to direct infrared radiation across the surface;
   an infrared camera configured to scan the surface and output a first signal proportional to emitted infrared radiation emitted by at least one of the surface and a first type of foreign object debris material, the emitted infrared radiation responsive to the infrared radiation from the thermal excitation source;
   a controller coupled to the thermal excitation source and to the infrared camera, the controller configured to compare the first signal from the infrared camera with a first threshold to detect presence of the first type of foreign object debris material; and
   a controllable nozzle coupled to a high pressure gas source and coupled to the controller, wherein the controller, in response to detection of the first type of foreign object debris material on the surface, directs gas through the controllable nozzle at the first type of foreign object debris material.

2. The system of claim 1, further comprising a layup machine to apply a layer of material to the surface, the layup machine configured to move along the surface, wherein the thermal excitation source, the infrared camera and the controllable nozzle are coupled to the layup machine.

3. The system of claim 1, further comprising a terminal coupled to the controller, the terminal including a display, and wherein the controller is further configured to provide an indication on the display upon detection of foreign object debris material.

4. The system of claim 1, further comprising:
   an ultraviolet light source configured to direct ultraviolet light across the surface;
   an ultraviolet light camera configured to scan the surface and output a second signal proportional to reflected ultraviolet light reflected by at least one of the surface and a second type of foreign object debris material, the reflected ultraviolet light responsive to the ultraviolet light from the ultraviolet light source; and
   wherein the controller, in response to detection of the second type of foreign object debris material based on a comparison of the second signal to a second threshold, directs gas through the controllable nozzle at the second type of foreign object debris material.

5. The system of claim 4, further comprising:
a visible light source configured to direct visible light across the surface;
a visible light camera configured to scan the surface and output a third signal proportional to reflected visible light reflected by at least one of the surface and a third type of foreign object debris material, the reflected visible light responsive to the visible light from the visible light source; and
wherein the controller, in response to detection of the third type of foreign object debris material based on a comparison of the third signal to a third threshold, directs gas through the controllable nozzle at the third type of foreign object debris material.

6. The system of claim 1, further comprising:
a visible light source configured to direct visible light across the surface;
a visible light camera configured to scan the surface and output a second signal proportional to reflected visible light reflected by at least one of the surface and a second type of foreign object debris material, the reflected visible light responsive to the visible light from the visible light source; and
wherein the controller, in response to detection of the second type of foreign object debris material based on a comparison of the second signal to a second threshold, directs gas through the controllable nozzle at the second type of foreign object debris material.

7. The system of claim 1, further comprising:
a conveyor to move the surface relative to a layup machine that applies a layer of material to the surface; and
a platform coupled to the thermal excitation source, the infrared camera, and the controllable nozzle.

8. The system of claim 1, wherein the surface is an outer surface of a composite part being formed by a composite layup machine.

9. The system of claim 1, further comprising:
a second infrared camera configured to scan the surface and output a second signal proportional to reflected infrared radiation reflected by at least one of the surface and a second type of foreign object debris material, the reflected infrared radiation responsive to the infrared radiation from the thermal excitation source; and
wherein the controller, in response to detection of the second type of foreign object debris material based on a comparison of the second signal to a second threshold, directs gas through the controllable nozzle at the second type of foreign object debris material.

10. A system for detection of foreign object debris material, the system comprising:
a thermal excitation source configured to direct infrared radiation across a surface, wherein the surface is an outer surface of a composite part being formed by a composite layup machine;
an infrared camera configured to scan the surface and output a first signal proportional to emitted infrared radiation emitted by at least one of the surface and a first type of foreign object debris material, the emitted infrared radiation responsive to the infrared radiation from the thermal excitation source; and
a controller coupled to the thermal excitation source and to the infrared camera, the controller configured to compare the first signal from the infrared camera with a first threshold to detect presence of the first type of foreign object debris material.

11. The system of claim 10, further comprising a controllable nozzle coupled to an air source, the controllable nozzle directed at the surface, and wherein the controller is further configured to cause the controllable nozzle to direct air at the surface upon detection of foreign object debris material.

12. The system of claim 10, further comprising a terminal coupled to the controller, the terminal including a display, and wherein the controller is further configured to provide an indication on the display upon detection of foreign object debris material.

13. The system of claim 10, further comprising:
an ultraviolet light source configured to direct ultraviolet light across the surface;
an ultraviolet light camera configured to scan the surface and output a second signal proportional to reflected ultraviolet light reflected by at least one of the surface and a second type of foreign object debris material, the reflected ultraviolet light responsive to the ultraviolet light from the ultraviolet light source; and
wherein the controller is configured to compare the second signal from the ultraviolet light camera with a second threshold to detect presence of the second type of foreign object debris material.

14. The system of claim 13, further comprising:
a visible light source configured to direct visible light across the surface;
a visible light camera configured to scan the surface and output a third signal proportional to reflected visible light reflected by at least one of the surface and a third type of foreign object debris material, the reflected visible light responsive to the visible light from the visible light source; and
wherein the controller is configured to compare the third signal from the visible light camera with a third threshold to detect presence of the third type of foreign object debris material.

15. The system of claim 10, further comprising:
a visible light source configured to direct visible light across the surface;
a visible light camera configured to scan the surface and output a second signal proportional to reflected visible light reflected by at least one of the surface and a second type of foreign object debris material, the reflected visible light responsive to the visible light from the visible light source; and
wherein the controller is configured to compare the second signal from the visible light camera with a second threshold to detect presence of the second type of foreign object debris material.

16. The system of claim 15, further comprising a conveyor to move the surface relative to the composite layup machine and a platform coupled to the thermal excitation source and the infrared camera.

17. The system of claim 10, wherein the controller is configured to record a location of detected foreign object debris material.

18. The system of claim 10, further comprising:
a second infrared camera configured to scan the surface and output a second signal proportional to reflected infrared radiation reflected by at least one of the surface and a second type of foreign object debris material, the reflected infrared radiation responsive to the infrared radiation from the thermal excitation source; and
wherein the controller is configured to compare the second signal from the second infrared camera with a second threshold to detect presence of the second type of foreign object debris material.

19. A method for detection of foreign object debris material on a surface, the method comprising:
- receiving a signal at a controller from an infrared camera, the signal proportional to emitted infrared radiation emitted by at least one of the surface and foreign object debris material, wherein the infrared camera scans the surface responsive to infrared radiation directed at the surface from a thermal excitation source;
- comparing, at the controller, the signal to a threshold to detect presence of the foreign object debris material; and
- in response to detection of the presence of the foreign object debris material, sending a command from the controller to cause a controllable nozzle to direct high pressure gas at the foreign object debris material.

20. The method of claim 19, further comprising recording locations of detected foreign object debris material.

21. A system for detection of foreign object debris material on a surface, the system comprising:
- a thermal excitation source configured to direct infrared radiation across the surface;
- a first infrared camera configured to scan the surface and output a first signal proportional to emitted infrared radiation emitted by at least one of the surface and a first type of foreign object debris material on the surface, the emitted infrared radiation responsive to the infrared radiation from the thermal excitation source;
- a second infrared camera configured to scan the surface and output a second signal proportional to reflected infrared radiation reflected by at least one of the surface and a second type of foreign object debris material on the surface, the reflected infrared radiation responsive to the infrared radiation from the thermal excitation source; and
- a controller coupled to the thermal excitation source, the first infrared camera, and the second infrared camera, the controller configured to compare the first signal with a first threshold to detect presence of the first type of foreign object debris material on the surface and to compare the second signal with a second threshold to detect presence of the second type of foreign object debris material on the surface.

\* \* \* \* \*